(12) United States Patent  
Reah et al.

(10) Patent No.: US 7,713,463 B1
(45) Date of Patent: May 11, 2010

(54) METHOD OF MANUFACTURING EMBROIDERED SURGICAL IMPLANTS

(75) Inventors: Christopher Reah, Taunton (GB); Alan McLeod, Somerset (GB)

(73) Assignee: NuVasive, Inc., San Diego, CA (US)

( * ) Notice: Subject to any disclaimer, the term of this patent is extended or adjusted under 35 U.S.C. 154(b) by 0 days.

(21) Appl. No.: 12/270,832

(22) Filed: Nov. 13, 2008

Related U.S. Application Data

(60) Provisional application No. 61/002,881, filed on Nov. 13, 2007.

(51) Int. Cl.
*B29C 67/00* (2006.01)

(52) U.S. Cl. .................... 264/490; 264/480; 264/413; 264/479; 264/489; 623/11.11; 623/23.72; 623/23.74

(58) Field of Classification Search ............... 264/405, 264/489, 490, 413, 479, 480
See application file for complete search history.

(56) References Cited

U.S. PATENT DOCUMENTS

| | | | | |
|---|---|---|---|---|
| 3,449,836 A | * | 6/1969 | Stephansen et al. | 34/259 |
| 4,265,954 A | * | 5/1981 | Romanek | 428/85 |
| 4,269,581 A | * | 5/1981 | Ury et al. | 425/174.4 |
| 4,274,209 A | | 6/1981 | Kawaguchi | |
| 4,393,671 A | | 7/1983 | Ito | |
| 4,919,659 A | * | 4/1990 | Horbett et al. | 427/2.25 |
| 5,055,242 A | * | 10/1991 | Vane | 264/463 |
| 5,318,650 A | * | 6/1994 | Kerawalla | 156/245 |
| 5,338,169 A | * | 8/1994 | Buckley | 425/82.1 |
| 5,364,258 A | * | 11/1994 | Buckley et al. | 425/501 |
| 5,447,077 A | | 9/1995 | Lautenschlager | |
| 5,711,857 A | | 1/1998 | Armstrong | |
| 5,843,311 A | | 12/1998 | Richter et al. | |
| 6,093,205 A | | 7/2000 | McLeod et al. | |
| 6,165,217 A | * | 12/2000 | Hayes | 623/11.11 |
| 7,214,225 B2 | | 5/2007 | Ellis et al. | |
| 7,326,433 B2 | * | 2/2008 | Stenzel | 427/2.1 |
| 7,338,531 B2 | | 3/2008 | Ellis et al. | |
| 2005/0171147 A1 | * | 8/2005 | Brown et al. | 514/310 |
| 2005/0222128 A1 | * | 10/2005 | Brown et al. | 514/218 |
| 2007/0128342 A1 | * | 6/2007 | Stenzel | 427/2.1 |
| 2007/0141106 A1 | * | 6/2007 | Bonutti et al. | 424/423 |

FOREIGN PATENT DOCUMENTS

| | | |
|---|---|---|
| EP | 1955748 A | 8/2008 |
| WO | 2005/092247 A1 | 10/2005 |
| WO | 2005/092248 A1 | 10/2005 |
| WO | 2006/133130 A2 | 12/2006 |
| WO | 2008/095038 A1 | 8/2008 |
| WO | 2008/100685 A2 | 8/2008 |
| WO | 2008/131310 A1 | 10/2008 |
| WO | 2009/006455 A1 | 1/2009 |

* cited by examiner

*Primary Examiner*—Joseph S Del Sole
*Assistant Examiner*—David N Brown, II
(74) *Attorney, Agent, or Firm*—Jonathan D. Spangler; Jay B. Bell

(57) ABSTRACT

A method for applying microwave techniques to embroidered surgical implants including using microwave technology in the process of acetate removal and using microwave technology in the process of drying implants.

13 Claims, 3 Drawing Sheets

METHOD OF MANUFACTURING EMBROIDERED SURGICAL IMPLANTS

CROSS REFERENCES TO RELATED APPLICATIONS

The present application is a nonprovisional patent application claiming benefit under 35 U.S.C. §119(e) from U.S. Provisional Application Ser. No. 61/002,881, filed on Nov. 13, 2007, the entire contents of which are hereby expressly incorporated by reference into this disclosure as if set forth fully herein. The present application also incorporates by reference the following patents and patent applications in their entireties: commonly owned and co-pending U.S. patent application Ser. No. 11/968,157, filed on Dec. 31, 2007 and entitled "Using Zigzags to Create Three-Dimensional Embroidered Structures;" U.S. Pat. No. 7,338,531, issued Mar. 4, 2208 and entitled "Textile Prosthesis;" U.S. Pat. No. 7,214,225, issued May 8, 2007 and entitled "Connector;" and PCT Application Serial No. PCT/US08/60944, filed Apr. 18, 2008 and entitled "Textile-Based Surgical Implant and Related Methods."

BACKGROUND OF THE INVENTION

I. Field of the Invention

The present invention relates generally to microwave techniques used in embroidery and, more particularly, to microwave techniques used in embroidered surgical implants.

II. Discussion of the Prior Art

Embroidered structures are created on substrates. Some substrates are designed to stay in place with the embroidered structure while other substrates are removed at some point during the embroidery process. More specifically, some substrates are removed through processes of dissolution. The dissolvable substrate may be formed from acetate or any other material suitable for use as a dissolvable embroidery substrate.

Substrate removal for embroidered surgical implants currently takes up to five hours in a Soxhlet extractor and requires significant quantities of solvent. The removal of the substrate requires the embroidered implants to be fully immersed in the solvent. Thus, long hours and large quantities of solvent are needed to achieve dissolution of the substrate when using a Soxhlet extractor. In addition, large quantities of implants are typically placed in a Soxhlet extractor at once for batch dissolution of the substrates. Since the solvent is dripping down from the upper portion of the Soxhlet extractor onto a pile of embroidered implants, the time that any particular embroidered implant is immersed in the solvent will vary according to its position within the pile.

Furthermore, conventional drying techniques for embroidered surgical implants, such as oven drying or air drying, are time-consuming. Using conventional drying can take hours to fully dry an implant, thus creating bottlenecks in the manufacturing process. In addition, oven drying of some devices could act as the ideal breeding ground for bacteria, making the device difficult to sterilize.

The present invention is directed at overcoming, or at least improving upon, the disadvantages of the prior art.

SUMMARY OF THE INVENTION

The present invention accomplishes this goal by utilizing microwave technology in the process of manufacturing embroidered surgical implants, thereby significantly decreasing the amount of time needed to mass produce textile-based implants. According to one embodiment of the present invention, microwave technology may be applied to dissolve a base substrate in an embroidered structure during the manufacturing process. According to a second embodiment of the present invention, microwave technology may be applied to dry surgical implants after the surgical implants have been manufactured. Utilizing microwave technology for substrate removal and for drying implants significantly reduces the time needed for those two processes and improves upon the quality of those two processes as well.

According to the method of manufacturing an embroidered surgical implant incorporating the use of microwave technology described herein, the first step is embroidering a plurality of textile fibers onto a substrate to form a structure, similar to that shown and described in commonly owned and co-pending U.S. patent application Ser. No. 11/968,157, filed on Dec. 31, 2007 and entitled "Using Zigzags to Create Three-Dimensional Embroidered Structures," the entire contents of which are hereby incorporated by reference in its entirety into this disclosure as if set forth fully herein. Further examples of textile-based surgical implants and processes of manufacturing textile-based surgical implants are found in U.S. Pat. No. 7,338,531, issued Mar. 4, 2208 and entitled "Textile Prosthesis," U.S. Pat. No. 7,214,225, issued May 8, 2007 and entitled "Connector," and PCT Application Serial No. PCT/US08/60944, filed Apr. 18, 2008 and entitled "Textile-Based Surgical Implant and Related Methods," the complete disclosures of each of which are hereby incorporated by reference in its entirety into this disclosure as if set forth fully herein.

By way of example only, the textile-based structure may be constructed from any of a variety of fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers. By way of example only, the dissolvable substrate may be formed from acetate or any other material suitable for use as a dissolvable embroidery substrate.

The second step of the method is dissolving the substrate. According to one embodiment of the present invention, microwave technology may be applied to this second step to dissolve the substrate in an embroidered structure. When microwave technology is applied to substrate removal, the dissolution process is expedited. For a reaction like substrate removal, increased heat in the solution will accelerate the rate of reaction.

Microwave substrate removal takes place in small pressure vessels within a radiation-safe enclosure. Each pressure vessel contains a quantity of solvent disposed therein. Since heat energy rapidly increases the rate of reaction, each pressure vessel only requires a small quantity of solvent (rather than the large quantity of solvent required when using a Soxhlet extractor). By way of example only, the solvent may be acetone or any other solution suitable for dissolving the base substrate of an embroidered structure. Each pressure vessel further contains a plurality of embroidered surgical implants loosely packed therein. The embroidered surgical implants each include an embroidered structure and substrate.

After the implants have been placed inside the pressure vessels with a predetermined quantity of solvent, the radiation-safe enclosure is sealed. The microwave technology is then utilized by passing microwave radiation through the pressure vessels. The microwave radiation may be applied for any amount of time suitable for effective dissolution of the substrate into the solvent.

When heat is applied to the pressure vessels by the enclosure, the temperature and pressure created within the pressure vessels immediately turns the liquid solvent into a vaporized solvent. During the vaporization of the solvent, the bulk of the substrates of the surgical implants disintegrate into the vapor almost instantaneously. The vaporized solvent quickly acts to dissolve any remaining substrate in the moments following vaporization. As opposed to using a Soxhlet extractor, the use of microwave technology considerably increases the pressure in each vessel, which advantageously increases the boiling point of the solvent. Increasing the temperature of the solvent during the dissolution step is beneficial in that it may considerably speed up the dissolution process due to the increased speed at which the solvent molecules are moving. Thus, with microwave technology, the dissolution process may take only minutes (instead of the long hours spent dissolving the substrate in a Soxhlet extractor).

The utilization of microwave technology also provides a more uniform exposure to the solvent, and more specifically the vaporized solvent. This is particularly beneficial during mass production of embroidered surgical implants because every implant will receive a more uniform exposure to the solvent due to the vaporized solvent being more ubiquitous within the pressure vessel, and each side/surface of the implant will receive a more uniform exposure to the solvent, thereby reducing the time needed to remove the substrate for any particular implant. Embroidered structures are generally relatively porous due to the nature of the embroidery process. Thus, vaporized solvent may more easily reach the substrate located in the interior of the implant than would a liquid solvent. As a result, applying microwave technology to substrate removal advantageously removes substrate that is nearly impossible to remove with a conventional Soxhlet extractor.

Although described herein as using microwave technology over a Soxhlet extractor, it will be appreciated that microwave technology may be used in conjunction with a Soxhlet extractor to dissolve the substrate. By way of example only, a microwave may be used to remove the majority of the substrate, including difficult to remove substrate. Subsequently, a Soxhlet extractor may be used to remove residual traces of the substrate.

After dissolving the substrate, the third step involves performing any additional manufacturing steps, for example including but not limited to manually folding, assembling, and/or stitching the embroidered structure into the final surgical implant. The fourth step involves washing the implant in order to remove any foreign material, such as bacteria, other microorganisms, tiny particles, and/or impurities. The fifth step involves drying the implant to help prevent bacteria growth, and prepare the implant for packaging prior to sterilization.

According to second embodiment of the present invention, microwave technology may be applied to the fifth step to dry surgical implants. By utilizing a microwave for drying implants, the manufacturing process is expedited. Drying implants with microwave technology occurs by excitation of the water molecules rapidly evaporating off of the implants. Due to the reduction in drying time, the overall queuing/planning time in upstream operations is decreased. As a result, mass production efforts are increased.

Another added benefit of applying microwave technology to textile-based structures, and particularly embroidered surgical implants, is the reduction and/or elimination of bacteria and other microorganisms that may be present in the implant during the manufacturing process. Since microwave radiation and/or heat can kill microbes, when applying microwave technology to embroidered implants, there may be a reduced likelihood of infection. Due to the large surface area of a fibrous textile material, microwave technology is an advantageous safety control.

After the implant is dried, the sixth step involves packing the implant into a suitable package or container. The container may include any container suitable for holding and transporting a textile-based surgical implant, for example including but not limited to a pouch, box, canister, jar, and the like. The last step involves sterilizing the implant and package. Sterilization of the implant and package may be accomplished through any suitable sterilization processes commonly known in the art, including but not limited to autoclaving (i.e. applying heat under pressure for a predetermined amount of time) and radiation treatment.

BRIEF DESCRIPTION OF THE DRAWINGS

Many advantages of the present invention will be apparent to those skilled in the art with a reading of this specification in conjunction with the attached drawings, wherein like reference numerals are applied to like elements and wherein.

DESCRIPTION OF THE PREFERRED EMBODIMENT

Illustrative embodiments of the invention are described below. In the interest of clarity, not all features of an actual implementation are described in this specification. It will of course be appreciated that in the development of any such actual embodiment, numerous implementation-specific decisions must be made to achieve the developers' specific goals, such as compliance with system-related and business-related constraints, which will vary from one implementation to another. Moreover, it will be appreciated that such a development effort might be complex and time-consuming, but would nevertheless be a routine undertaking for those of ordinary skill in the art having the benefit of this disclosure. The microwave techniques for embroidery disclosed herein boasts a variety of inventive features and components that warrant patent protection, both individually and in combination.

Figure 1:
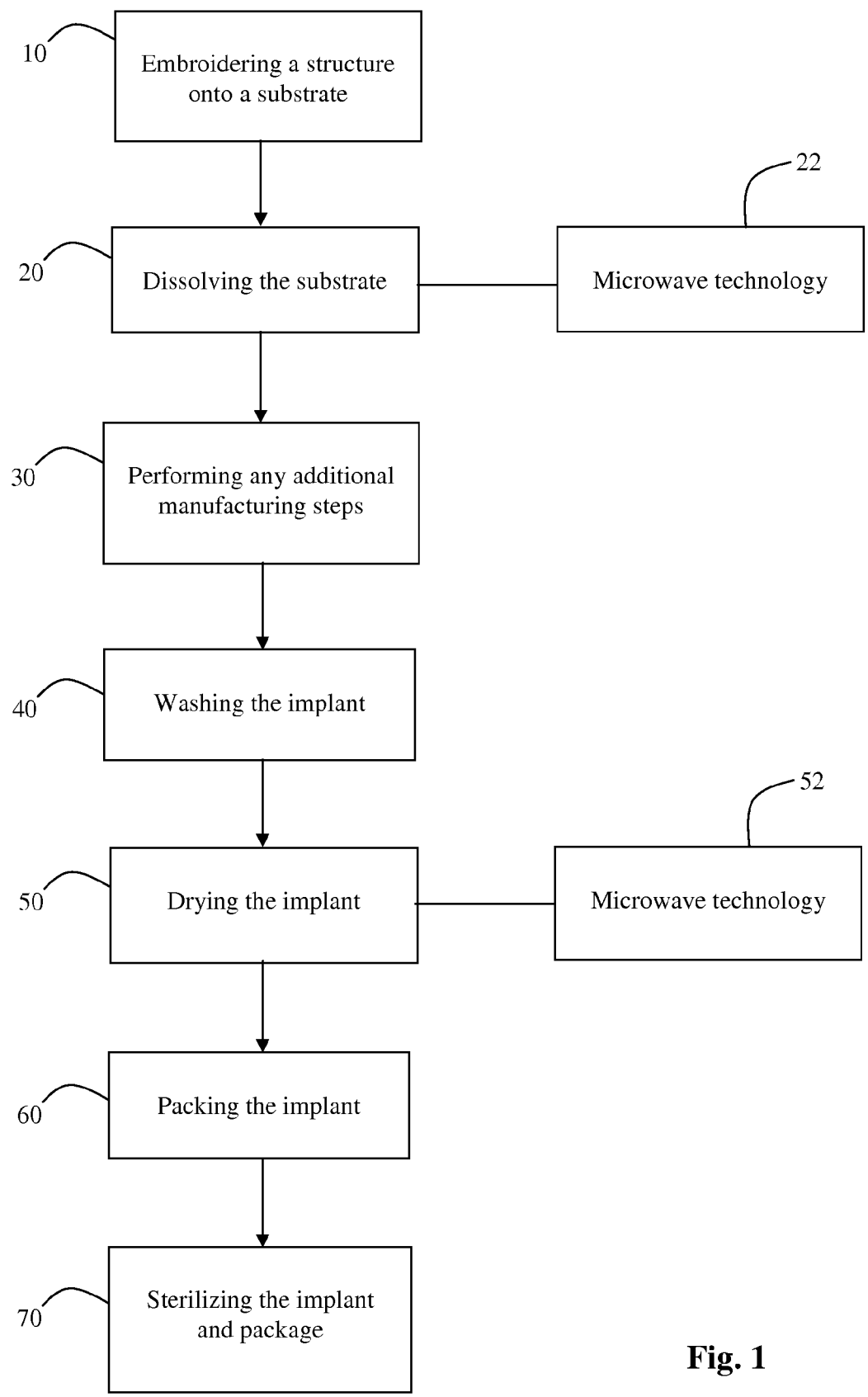
FIG. 1 is a flow chart illustrating a process of creating an embroidered surgical implant according to the present invention.

FIG. 1 is a flow chart illustrating the general process of creating an embroidered surgical implant incorporating the use of microwave technology according to the present invention. The first step 10 is embroidering a plurality of textile fibers onto a substrate to form a structure, similar to that shown and described in commonly owned and co-pending U.S. patent application Ser. No. 11/968,157, filed on Dec. 31, 2007 and entitled "Using Zigzags to Create Three-Dimensional Embroidered Structures," the entire contents of which are hereby incorporated by reference in its entirety into this disclosure as if set forth fully herein. Further examples of textile-based surgical implants and processes of manufacturing textile-based surgical implants are found in U.S. Pat. No.

7,338,531, issued Mar. 4, 2208 and entitled "Textile Prosthesis," U.S. Pat. No. 7,214,225, issued May 8, 2007 and entitled "Connector," and PCT Application Serial No. PCT/US08/60944, filed Apr. 18, 2008 and entitled "Textile-Based Surgical Implant and Related Methods," the complete disclosures of each of which are hereby incorporated by reference in its entirety into this disclosure as if set forth fully herein.

By way of example only, the textile-based structure may be constructed from any of a variety of fibrous materials, for example including but not limited to polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers. By way of example only, the dissolvable substrate may be formed from acetate or any other material suitable for use as a dissolvable embroidery substrate.

The second step 20 is dissolving the substrate. According to one embodiment of the present invention, microwave technology 22 may be applied to this second step 20 to dissolve the substrate in an embroidered structure. When microwave technology is applied to substrate removal, the dissolution process is expedited. For a reaction like substrate removal, increased heat in the solution will accelerate the rate of reaction.

Figure 2:
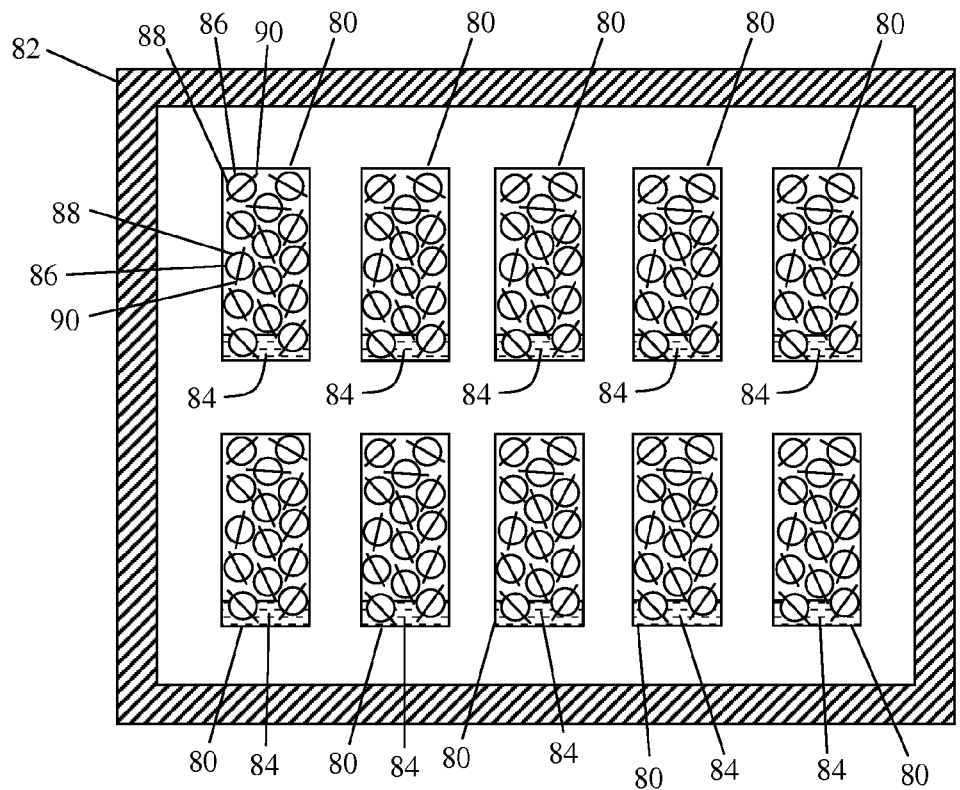
FIG. 2 is a cross-sectional view of a microwave including a plurality of pressure vessels, each containing a number of embroidered surgical implants and a solvent prior to applying heat according to one step of the process of FIG. 1.
Figure 3:
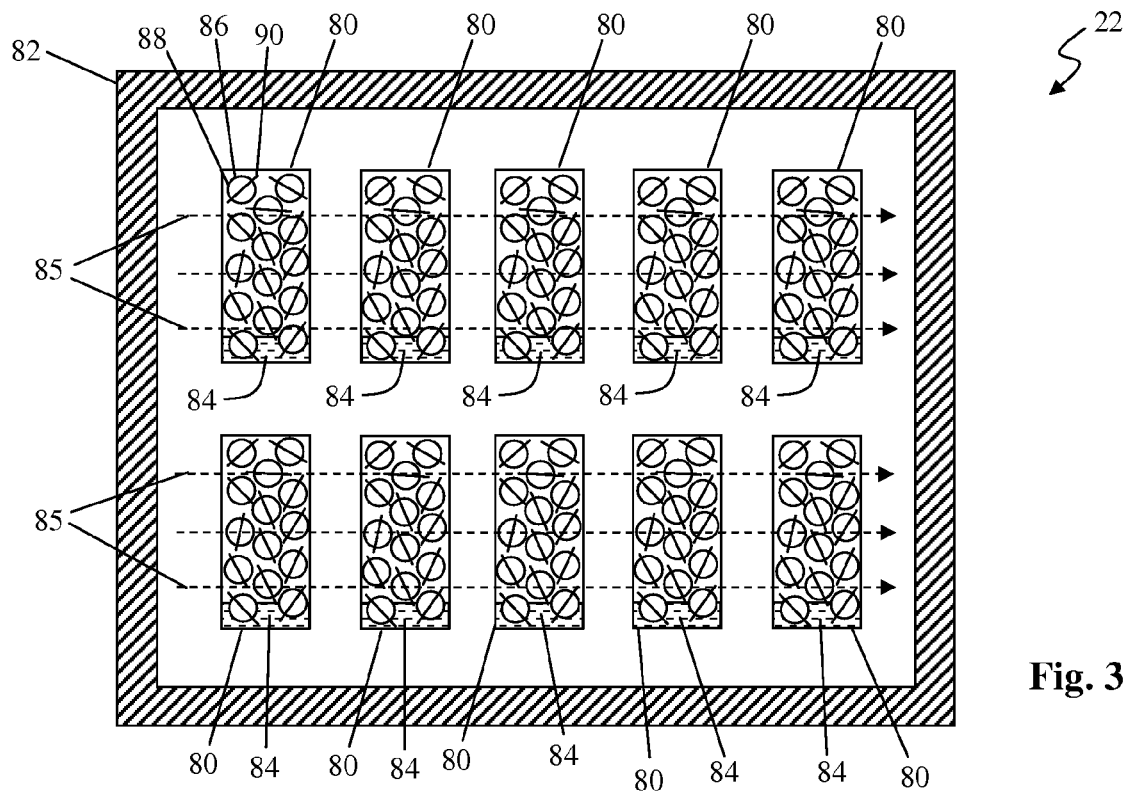
FIG. 3 is a cross-sectional view of the microwave of FIG. 3 during application of microwave radiation.

FIGS. 2 and 3 illustrate the use of microwave technology 22 during the second step 20 of dissolving the substrate in an embroidered structure. Referring to FIG. 2, microwave substrate removal takes place in small pressure vessels 80 within a radiation-safe enclosure 82. For the purposes of illustration only, the example of the radiation-safe enclosure 82 shown and described herein includes ten pressure vessels 80 disposed therein, however the radiation-safe enclosure 82 may be provided with any number of pressure vessels 80 positioned in any arrangement within the enclosure 82 without departing from the scope of the present invention. Each pressure vessel 80 contains a quantity of solvent 84 disposed therein. Since heat energy rapidly increases the rate of reaction, each pressure vessel 80 only requires a small quantity of solvent 84 (rather than the large quantity of solvent required when using a Soxhlet extractor). By way of example only, the solvent 84 may be acetone or any other solution suitable for dissolving the base substrate of an embroidered structure.

Each pressure vessel 80 further contains a plurality of embroidered surgical implants 86 loosely packed therein. By way of example only, the pressure vessels 80 are shown in FIG. 2 as containing fourteen implants 86 each, however the pressure vessels 80 may be sized to accommodate any number of embroidered surgical implants 86 without departing from the scope of the present invention. The embroidered surgical implants 86 each include an embroidered structure 88 and substrate 90.

Referring to FIG. 3, after the implants 86 have been placed inside the pressure vessels 80 with a predetermined quantity of solvent 84, the radiation-safe enclosure 82 is sealed. The microwave technology is then utilized by passing microwave radiation 85 through the pressure vessels 80. The microwave radiation 85 may be applied for any amount of time suitable for effective dissolution of the substrate into the solvent 84.

Figure 4:
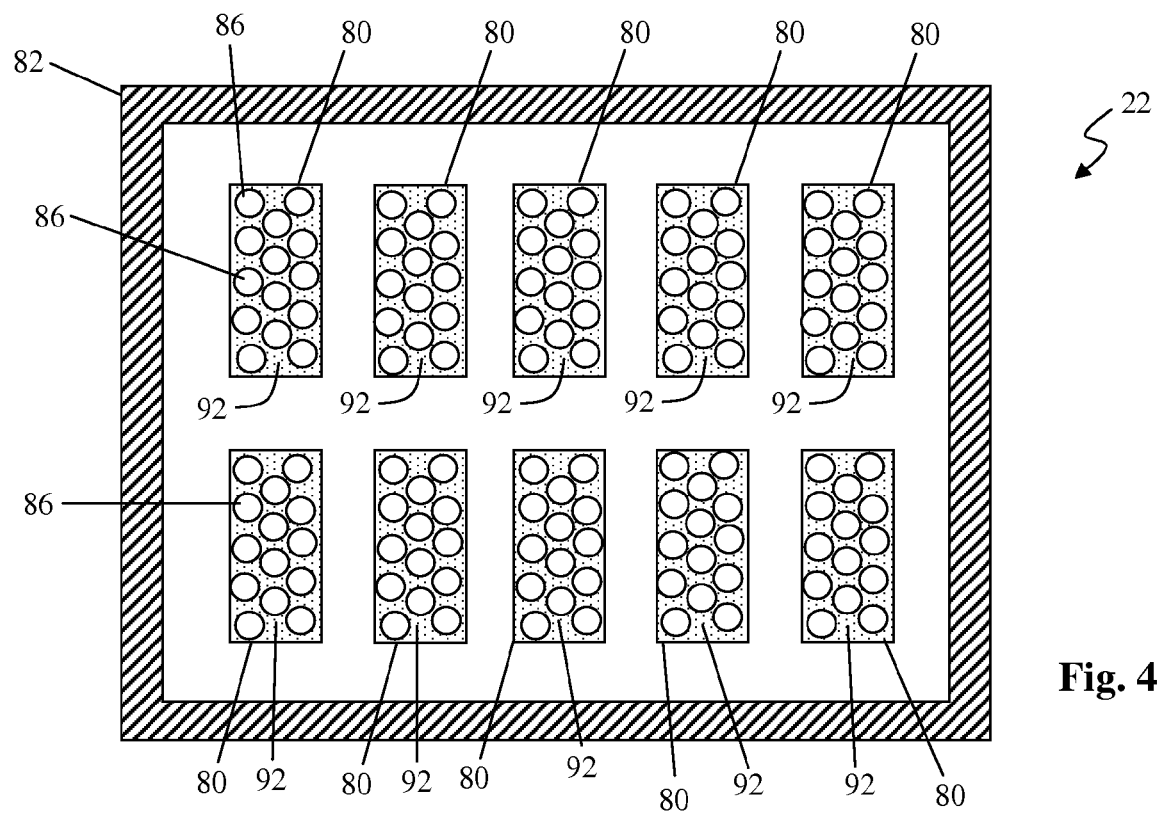
FIG. 4 is a cross-sectional view of the microwave of FIG. 2 after applying heat according to one step of the process of FIG. 1.

Referring now to FIG. 4, the radiation-safe enclosure 82 of FIG. 2 is illustrated after the pressure vessels 80 have been heated. When heat is applied to the pressure vessels 80 by the enclosure 82, the temperature and pressure created within the pressure vessels 80 immediately turns the liquid solvent 84 into a vaporized solvent 92. During the vaporization of the solvent 84, the bulk of the substrates 90 of the surgical implants 86 disintegrate into the vapor almost instantaneously. The vaporized solvent 92 quickly acts to dissolve any remaining substrate 90 in the moments following vaporization. As opposed to using a Soxhlet extractor, the use of microwave technology 22 considerably increases the pressure in each vessel, which advantageously increases the boiling point of the solvent 84. Increasing the temperature of the solvent during the dissolution step is beneficial in that it may considerably speed up the dissolution process due to the increased speed at which the solvent molecules are moving. Thus, with microwave technology 22, the dissolution process may take only minutes (instead of the long hours spent dissolving the substrate in a Soxhlet extractor).

The utilization of microwave technology 22 also provides a more uniform exposure to the solvent 84, and more specifically the vaporized solvent 92. This is particularly beneficial during mass production of embroidered surgical implants 86 because every implant will receive a more uniform exposure to the solvent due to the vaporized solvent 92 being more ubiquitous within the pressure vessel 80, and each side/surface of the implant 86 will receive a more uniform exposure to the solvent 92, thereby reducing the time needed to remove the substrate for any particular implant. Embroidered structures are generally relatively porous due to the nature of the embroidery process. Thus, vaporized solvent 92 may more easily reach the substrate located in the interior of the implant 86 than would a liquid solvent 84. As a result, applying microwave technology to substrate removal advantageously removes substrate that is nearly impossible to remove with a conventional Soxhlet extractor.

Although described herein as using microwave technology 22 over a Soxhlet extractor, it will be appreciated that microwave technology 22 may be used in conjunction with a Soxhlet extractor to dissolve the substrate 90. By way of example only, a microwave 82 may be used to remove the majority of the substrate 90, including difficult to remove substrate 90. Subsequently, a Soxhlet extractor may be used to remove residual traces of the substrate 90.

After dissolving the substrate, the third step 30 involves performing any additional manufacturing steps, for example including but not limited to manually folding, assembling, and/or stitching the embroidered structure into the final surgical implant. The fourth step 40 involves washing the implant in order to remove any foreign material, such as bacteria, other microorganisms, tiny particles, and/or impurities. The fifth step 50 involves drying the implant to help prevent bacteria growth, and prepare the implant for packaging prior to sterilization.

According to second embodiment of the present invention, microwave technology 52 may be applied to the fifth step 50 to dry surgical implants. By utilizing a microwave for drying implants, the manufacturing process is expedited. Drying implants with microwave technology occurs by excitation of the water molecules rapidly evaporating off of the implants. Due to the reduction in drying time, the overall queuing/planning time in upstream operations is decreased. As a result, mass production efforts are increased.

Another added benefit of applying microwave technology to textile-based structures, and particularly embroidered surgical implants, is the reduction and/or elimination of bacteria and other microorganisms that may be present in the implant during the manufacturing process. Since microwave radiation and/or heat can kill microbes, when applying microwave technology to embroidered implants, there may be a reduced likelihood of infection. Due to the large surface area of a fibrous textile material, microwave technology is an advantageous safety control.

After the implant is dried, the sixth step 60 involves packing the implant into a suitable package or container. The container may include any container suitable for holding and transporting a textile-based surgical implant, for example including but not limited to a pouch, box, canister, jar, and the like. The last step 70 involves sterilizing the implant and package. Sterilization of the implant and package may be accomplished through any suitable sterilization processes commonly known in the art, including but not limited to autoclaving (i.e. applying heat under pressure for a predetermined amount of time) and radiation treatment.

While the invention is susceptible to various modifications and alternative forms, specific embodiments thereof have been shown by way of example in the drawings and are herein described in detail. It should be understood, however, that the description herein of specific embodiments is not intended to limit the invention to the particular forms disclosed, but on the contrary, the invention is to cover all modifications, equivalents, and alternatives falling within the spirit and scope of the invention as defined herein.

What is claimed is:

1. A method of manufacturing a surgical implant, comprising the steps of:
   embroidering a plurality of biocompatible textile filaments onto a substrate along a predetermined pathway to create an embroidered structure;
   placing said embroidered structure within a container, said container including a liquid solvent;
   placing said container including said embroidered structure and said liquid solvent within a radiation-safe enclosure; and
   applying microwave radiation to said embroidered structure such that said microwave radiation passes through said embroidered structure and is contained within said enclosure;
   wherein said step of applying microwave radiation causes said liquid solvent to vaporize into a solvent vapor, and said solvent vapor causes near instantaneous dissolution of at least a substantial portion of the substrate.

2. The method of claim 1, wherein said container comprises a pressure vessel dimensioned to hold a plurality of embroidered structures therein.

3. The method of claim 2, wherein said radiation-safe enclosure is dimensioned to receive a plurality of pressure vessels disposed therein.

4. The method of claim 1, wherein said textile filament comprises at least one of polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers.

5. The method of claim 1, further comprising the steps of:
   washing the implant in order to remove any foreign material; and
   drying the implant to prevent bacteria growth within the implant.

6. The method of claim 5, wherein the step of drying the implant comprises applying microwave radiation to said implant.

7. A method of manufacturing a surgical implant, comprising the steps of:
   embroidering a plurality of biocompatible textile filaments onto a substrate along a predetermined pathway to create at least one biocompatible structure attached to said substrate;
   sealing said at least one biocompatible structure including the attached substrate into a first container, said first container having a solvent disposed therein;
   sealing said first container within a second container;
   applying microwave radiation to said first container such that said microwave radiation passes through said first container and said structure and is contained within said second container, said microwave radiation effecting a change in state of the solvent from a liquid solvent to a vapor solvent, said microwave radiation further effecting an increase in temperature and pressure within said first container such that said vapor solvent rapidly dissolves said substrate; and
   removing said biocompatible structure from said first and second containers.

8. The method of claim 7, further comprising the steps of:
   washing the implant in order to remove any foreign material; and
   drying the implant to prevent bacteria growth within the implant.

9. The method of claim 8, wherein the step of drying the implant comprises
   applying microwave radiation to said implant.

10. The method of claim 7, further comprising the step of:
    performing additional manufacturing steps including at least one of manually folding, assembling, and stitching the embroidered structure into a final surgical implant.

11. The method of claim 7, wherein said textile filament comprises at least one of polyester fiber, polypropylene, polyethylene, ultra high molecular weight polyethylene (UHMWPe), poly-ether-ether-ketone (PEEK), carbon fiber, glass, glass fiber, polyaramide, metal, copolymers, polyglycolic acid, polylactic acid, biodegradable fibers, silk, cellulosic and polycaprolactone fibers.

12. The method of claim 7, wherein said first container comprises a pressure vessel dimensioned to hold a plurality of biocompatible structures therein.

13. The method of claim 12, wherein said second container is dimensioned to receive a plurality of pressure vessels disposed therein.

* * * * *